US006341521B1

(12) United States Patent
Bartolomey et al.

(10) Patent No.: US 6,341,521 B1
(45) Date of Patent: Jan. 29, 2002

(54) PROCESS AND DEVICE FOR MEASURING THE AMOUNT OF IMPURITIES IN A GAS SAMPLE TO BE ANALYZED

(75) Inventors: Mélanie Bartolomey; Jean-Marc Girard, both of Paris; Patrick Mauvais, Villepreux, all of (FR); James McAndrew, Lockport, IL (US)

(73) Assignee: L'Air Liquide, Societe Anonyme pour l'Etude et l'Exploitation des Procedes Georges Claude, Paris (FR)

(*) Notice: Subject to any disclaimer, the term of this patent is extended or adjusted under 35 U.S.C. 154(b) by 0 days.

(21) Appl. No.: 09/416,758

(22) Filed: Oct. 12, 1999

(30) Foreign Application Priority Data

Oct. 16, 1998 (FR) .............................. 98 13013

(51) Int. Cl.[7] ...................... G01N 21/11; G01N 21/31; G01N 21/35; G01N 21/39
(52) U.S. Cl. ................. 73/31.03; 73/24.02; 73/24.04; 73/24.06; 250/339.13
(58) Field of Search .......................... 73/24.02, 24.04, 73/24.06, 31.03; 250/339.13

(56) References Cited

U.S. PATENT DOCUMENTS

| 5,506,685 A |   | 4/1996 | Grasdepot |
|---|---|---|---|
| 5,705,816 A | * | 1/1998 | Ronge et al. ............... 250/343 |
| 5,821,537 A |   | 10/1998 | Ishihara et al. ........ 250/339.13 |
| 6,154,284 A | * | 11/2000 | McAndrew et al. ........ 356/437 |

FOREIGN PATENT DOCUMENTS

| CA | 2064540 | * 10/1992 | ................ 73/24.02 |
|---|---|---|---|
| EP | 0 387 684 | 9/1990 | |
| EP | 0 509 249 | 10/1992 | ................ 73/24.02 |

OTHER PUBLICATIONS

May et al, "Data Processing and Calibration for Tunable Diode Laser Harmonic Absorption Spectrometers,"*J. Quant. Spectros. Radiat. Transfer*, vol. 49, No. 4, pp. 335–347 (1993).
Webster et al, *Laser Remote Chemical Analysis*, Wiley NY pp. 178–187 (1988).

* cited by examiner

*Primary Examiner*—Daniel S. Larkin
(74) *Attorney, Agent, or Firm*—Burns, Doane, Swecker & Mathis, L.L.P.

(57) ABSTRACT

Provided is a process for measuring the amount of impurities in a gas sample filling a laser absorption spectroscopy analysis cell. The process includes calculating the value of a characteristic representative of the absorbance of the gas sample, from a measurement of the gas sample at a single given pressure, and quantifying the impurities on the basis of a predetermined law for the variation of the characteristic as a function of the amount of impurities. The characteristic is the ratio of the difference between the luminous intensity ($I_{ana}$) of a light beam transmitted through the gas and the luminous intensity ($I_{ref}$) of the incident beam to the luminous intensity ($I_{ref}$) of the incident beam. The impurities are quantified on the basis of a value of the coefficient of proportionality between the amount of impurities and the characteristic, determined on the basis of a table of variation of the characteristic as a function of pressure, for a given amount of impurities.

21 Claims, 2 Drawing Sheets

PROCESS AND DEVICE FOR MEASURING THE AMOUNT OF IMPURITIES IN A GAS SAMPLE TO BE ANALYZED

BACKGROUND OF THE INVENTION

1. Field of the Invention

The present invention relates to a process and to a device making it possible to measure the amount of impurities present in the trace state in a gas sample to be analysed, and in particular to a measurement process and device using a technique of analysis by laser absorption spectroscopy It is especially suitable for detecting the water content or water vapour content of gases conventionally used in the field of the fabrication of microelectronic components.

2. Description of Related Art

Among volatile contaminants, moisture would appear to be the most harmful, by reason of the interactions which it can develop with the surfaces which it is liable to encounter, thus rendering it especially difficult to eliminate. Furthermore, the presence of water in reactive gases may give rise to serious damage in gas distribution networks.

There are at present several techniques for measuring the amount of moisture present in gases Such techniques generally require the use of relatively expensive and voluminous equipment and are relatively lengthy to implement, thus greatly limiting their effectiveness.

An effective technique for detecting traces of water vapour in gases consists of the technique of analysis by infrared laser absorption spectroscopy, also known as "TDLAS".

According to this technique, the sample of gas to be analysed is placed in an analysis cell and is illuminated by light emitted by a diode according to a wavelength corresponding to the wavelength at which the absorption of light by the impurities is a maximum Thus, for quantifying the water molecules present in the gas to be analysed, the laser ray is emitted according to a wavelength of $1.368\mu$.

According to the technique of analysis by laser absorption spectroscopy, the laser ray is divided into two beams, namely an analysis beam which passes through the analysis cell and a reference beam.

Each of the beams is thereafter detected with the aid of photodiodes.

The actual quantification of the water molecules, performed by means of an analyser operating according to this technique, is based on the Beer-Lambert law, the equation for which is as follows:

$$I_{ana} = I_{ref} \times \exp(-K.N_{nH2O}.L) \quad (1)$$

in which:

$N_{nH2O}$ represents the concentration of molecules of impurities, $I_{ref}$ represents the intensity of the reference beam on entry to the analysis cell, $I_{ana}$ denotes the intensity of the analysis beam, K denotes the molecular transmission coefficient, which depends on the type of gas and on its pressure, and L denotes the optical path length travelled by the analysis beam through the cell.

In practice, quantification of the impurity molecules requires a prior step of calibrating the analyser so as to ascertain the value of the coefficient K, at the relevant pressure and for the type of gas analysed, the concentration of impurities being evaluated thereafter on the basis of the difference between the intensity of the analysis beam and the intensity of the reference beam.

The prior calibration step consists, for each type of gas and for a given value of pressure, in defining the zero of the analyser by analysing a dry gas and then in computing a calibration curve by carrying out metered additions of water to the dry gas.

Such calibration, which must be performed periodically, is relatively lengthy and tedious to implement. It is furthermore liable to give rise to errors in so far as it may be subject to pollution. Furthermore, the analyser must be accompanied by a specific setup for calibration, thus rendering it relatively voluminous.

SUMMARY OF THE INVENTION

The purpose of the invention is to alleviate these drawbacks and to provide a device and a process for measuring the amount of impurities in a gas sample capable of directly delivering a measurement of the concentration of impurities.

Its subject is therefore a process for measuring the amount of impurities in a gas sample filling a laser absorption spectroscopy analysis cell, consisting in calculating the value of a characteristic representative of the absorbance of the gas sample, at a given pressure, and quantifying the impurities on the basis of a predetermined law for the variation of the characteristic as a function of the amount of impurities, characterized in that the said characteristic consists of a quantity which varies linearly at constant pressure as a function of the amount of impurities, the impurities being quantified on the basis of a value of a coefficient of proportionality between the amount of impurities and the characteristic, determined on the basis of a table of variation of the said characteristic as a function of pressure, for a given amount of impurities.

The process according to the invention can furthermore comprise one or more of the following characteristics, taken in isolation or according to all the technically possible combinations:

the said characteristic consists of the ratio between, on the one hand, the difference between the luminous intensity of the light beam transmitted through the gas sample and the luminous intensity of the incident beam and, on the other hand, the intensity of the incident beam;

the light beam is emitted by means of a diode laser according to a range of wavelengths encompassing the wavelength at which the absorption of light by the said impurities is a maximum;

the light beam emitted by the diode laser is divided into a first analysis beam intended to pass through the cell and a reference beam, the luminous intensity of the incident beam being measured by measuring the intensity of the reference beam;

the table of variation of the said characteristic is computed for various types of gas to be analysed, by measuring the value of the said characteristic at various pressures, for a gas containing a predetermined amount of impurities;

the impurities comprise water or water vapour; and the gas to be analysed is chosen from gases used in the field of the fabrication of microelectronic components, such as $NH_3$, $HCl$, $HBr$, $HF$, $NO$, $SiH_4$, $GeH_4$, and perfluorocarbonated gases.

The subject of the invention is also a device for measuring the amount of impurities in a gas sample for the implementation of a process as defined above, comprising a diode laser intended for emitting a light beam according to a range of wavelengths encompassing the wavelength at which the absorption of light by the said impurities is a maximum, a light splitter facility adapted for dividing the emitted beam into an analysis beam intended to be transmitted through a laser absorption spectroscopy analysis cell filled with the gaseous sample to be analysed, and into a reference beam, photodetector means intended to receive the analysis and reference beams, and calculation means adapted for calculating the value of a characteristic varying linearly as a function of the amount of impurities and representative of the absorbance of the gas sample, on the basis of a comparison between the intensity, detected by the photodetector means, of the measurement and reference beams, and the calculation means include, stored in memory, a set of at least one table of variation of the said characteristic as a function of pressure for a given amount of impurities, with a view to the computation, on the basis of the said table, of the coefficient of proportionality to be applied to the calculated value of the said characteristic to obtain the amount of impurities.

Advantageously, the device includes, stored in memory, a set of tables each corresponding to a type of gas to be analysed.

BRIEF DESCRIPTION OF THE FIGURES OF THE DRAWING

Other characteristics and advantages will emerge from the following description given merely by way of example, and provided with reference to the appended drawings in which.

DETAILED DESCRIPTION OF THE PREFERRED EMBODIMENTS

Figure 1:
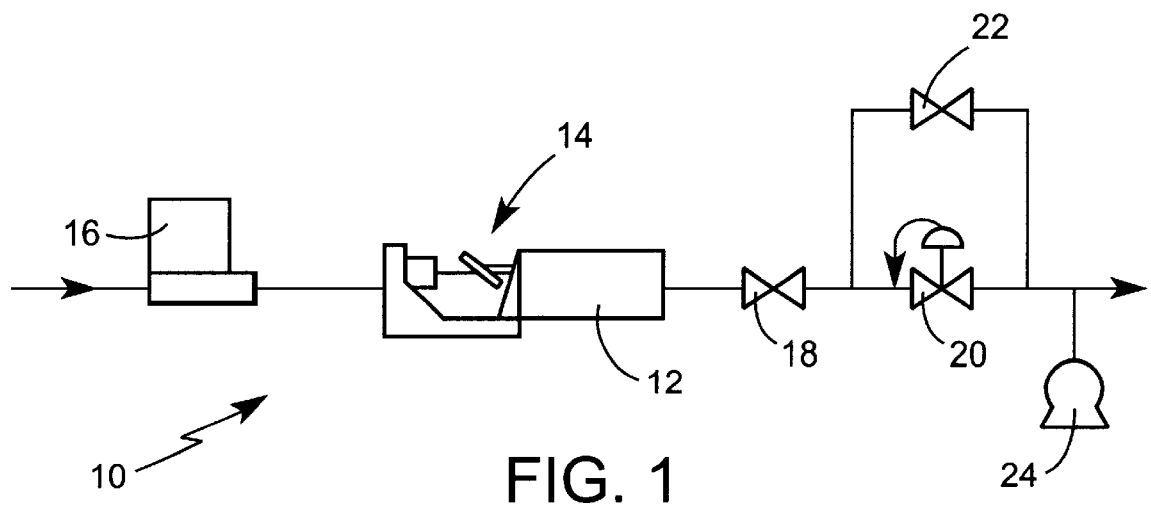
FIG. 1 is a schematic view of a measurement device according to the invention.

Represented in FIG. 1 is a measurement device in accordance with the invention, denoted by the general numerical reference 10.

In the exemplary embodiment considered, this device is intended to quantify water molecules present in a gas sample to be analysed filling an analysis cell 12 of a hygrometer 14.

Of course, the invention is not limited to the determination of the moisture content of a gas, but applies equally to the analysis of any other types of impurities present in the trace state in a gas sample and whose content is to be determined.

As may be seen in FIG. 1, the device 10 comprises, at input, a mass flow rate regulator 16 allowing adjustment of the gas flow rate fed to the hygrometer 14.

The regulator 16 is a regulator of conventional type adapted for the use envisaged. It will therefore not be described in detail hereinafter.

The hygrometer 14 is linked, at output, to a set of valves, namely a shutoff valve 18 and a pressure regulating valve 20 which is arranged in series with the shutoff valve 18.

A branch pipe controlled by a second shutoff valve 22 runs either side of the regulating valve 20.

Lastly, a chemical pump 24 capable of controlling the pressure of the gas filling the analysis cell 12, jointly with the regulating valve 20, is stationed at the outlet of the latter. The pump 24 is also a pump of conventional type and will therefore not be described in detail hereinafter.

It will however be noted that it is for example capable of regulating, jointly with the regulating valve 20, the pressure in the analysis cell 12 within a range extending from 50 mbar to 500 mbar.

Figure 2:
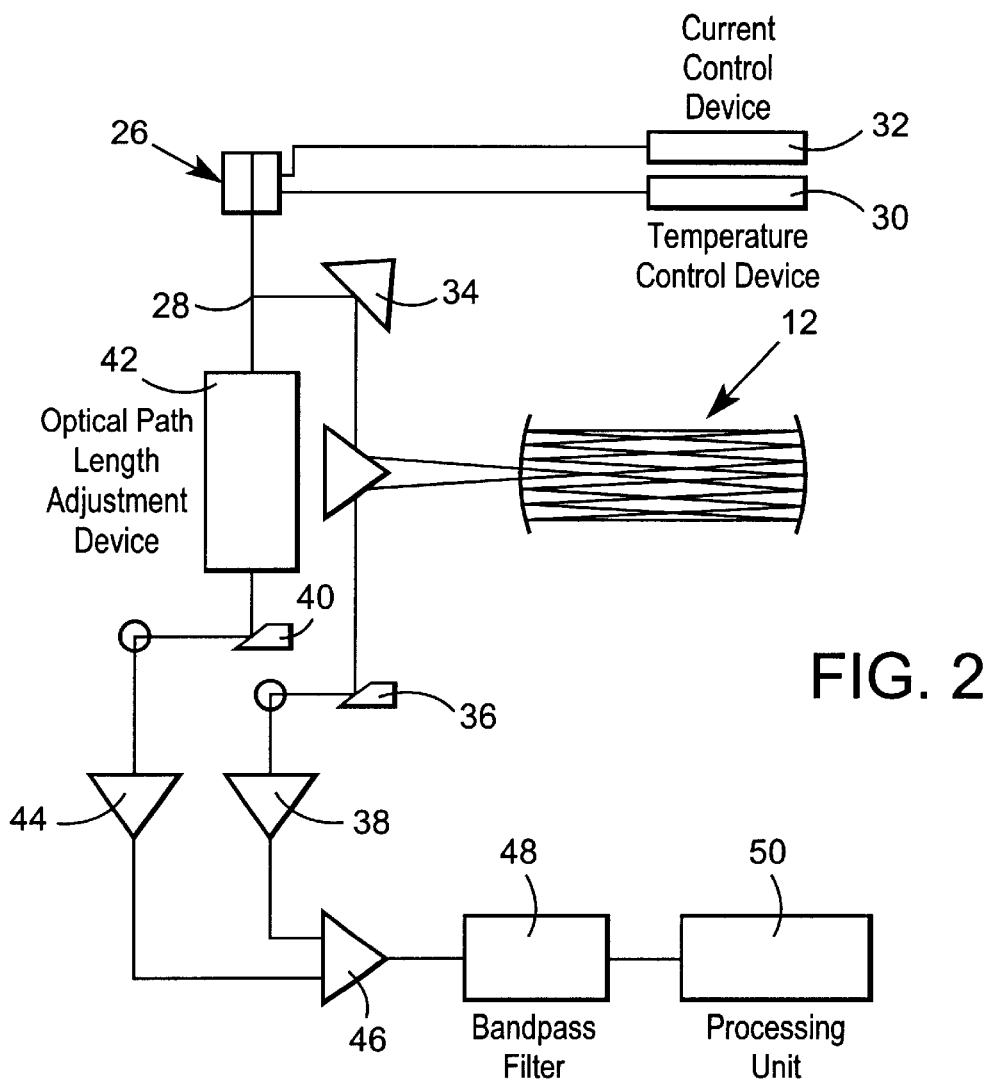
FIG. 2 is a schematic representation of a hygrometer entering into the construction of the device of FIG. 1.

With reference to FIG. 2, in which the analysis cell 12 has been represented schematically, the hygrometer 14 comprises a diode laser 26 emitting a light beam towards a light splitter facility 28 according to a wavelength range encompassing the wavelength at which the absorption of light by the water molecules is a maximum, that is to say 1.368 $\mu$m The diode 26 is linked to a temperature control device 30, with a view to maintaining the temperature of the diode constant, as well as to a diode supply current control device 32 adapted for feeding a sawtooth-shaped supply current so as to cause the emission of a radiation according to a range of wavelengths encompassing the wavelength at which the absorption of light by the impurities to be quantified is a maximum.

A first beam, constituting a measurement beam, is directed, with the aid of mirrors such as 34, towards the cell 12 around which it travels along numerous routes.

The light beam output by the cell 12 is detected by means of a first photodetector 36 linked at output to an amplifier 38.

Moreover, the second part of the divided beam, constituting a reference beam, is detected by a second photodetector 40 after passing through an optical path length adjustment device 42, so as to render the optical path lengths of the measurement beam and of the reference beam identical The signal delivered by the second photodetector 40 is thereafter amplified by means of a second amplifier 44.

The signals output by the first and second amplifiers 38 and 44 are thereafter input to a comparator 46 so as to be compared and then input to a bandpass filter 48, so as to eliminate the measurement noise.

Lastly, as may be seen in this FIG. 2, the filter 48 is linked to a processing unit 50 adapted for calculating, on the basis of the measured difference between the intensity of the analysis beam and the intensity of the reference beam, the concentration of water molecules present in the gas sample analysed.

To do this, the processing unit 50 computes a characteristic representative of the absorbance of the gas sample, varying linearly at constant pressure as a function of the amount of water molecules of the gas, and whose variation as a function of pressure, for a fixed amount of impurity molecules, is known.

This variation as a function of pressure is given in the form of a set of tables stored in memory, each corresponding to a type of gas capable of being analysed by the hygrometer 14, and giving the variation in the characteristic as a function of pressure, for a given amount of impurities.

The characteristic computed consists of the ratio between, on the one hand the difference between the intensity of the analysis beam and the intensity of the reference beam and, on the other hand, the intensity of the reference beam.

Indeed, referring again to the Beer-Lambert law mentioned earlier and given by the relation (1), and taking into account the particularly small measured quantities, this law can be approximated by the following relation by using first-order bounded expansions:

$$\frac{I_{ana} - I_{ref}}{I_{ref}} = K \cdot N_{nH2O} \cdot L \quad (2)$$

Moreover, taking into account the concentration of water molecules in the sample gas and of the ideal gas law, the relation defined above can be modified as follows:

$$\frac{I_{ana} - I_{ref}}{I_{ref}} = K \cdot L \cdot n_{ppb} \cdot 10^{-9} \frac{PV}{kT} \quad (3)$$

in which:

k denotes Boltzman's constant, $n_{ppb}$ denotes the content in ppb of the water molecules, V denotes the volume of the measurement cell 12; and T denotes the temperature of the gas.

It will be noted that the optical path length L, as well as the internal volume of the analysis cells are fixed once and for all through the construction of the apparatus. Additionally, the temperature of the analysis cell 12 is maintained constant by means of the temperature control device 30.

Under these conditions, for a given type of gas and for a given pressure, the quotient $(I_{ana}-I_{ref})/I_{ref}$ is directly proportional to the water vapour concentration, and is totally independent of any external parameter which might impair the signal delivered by the comparator 46.

For the quantification of the impurity molecules, the value of the characteristic corresponding to the analysis pressure P is extracted by the processing unit 50 from the stored tables, this value constituting, to within the ratio of the number of impurity molecules, the value of the coefficient of proportionality between the amount of impurities to be determined and the value of the characteristic $\Delta I/I_0$ calculated in the course of the analysis.

That is to say, for the determination of the value of the coefficient of proportionality, the value extracted from the tables should be divided by the amount of impurity contained in the gaseous sample used to compute the tables.

Thus, in so far as the characteristic calculated in the course of the analysis varies linearly as a function of the concentration of impurities, this concentration can be obtained directly on the basis of the coefficient of proportionality extracted from the tables.

Figure 3:
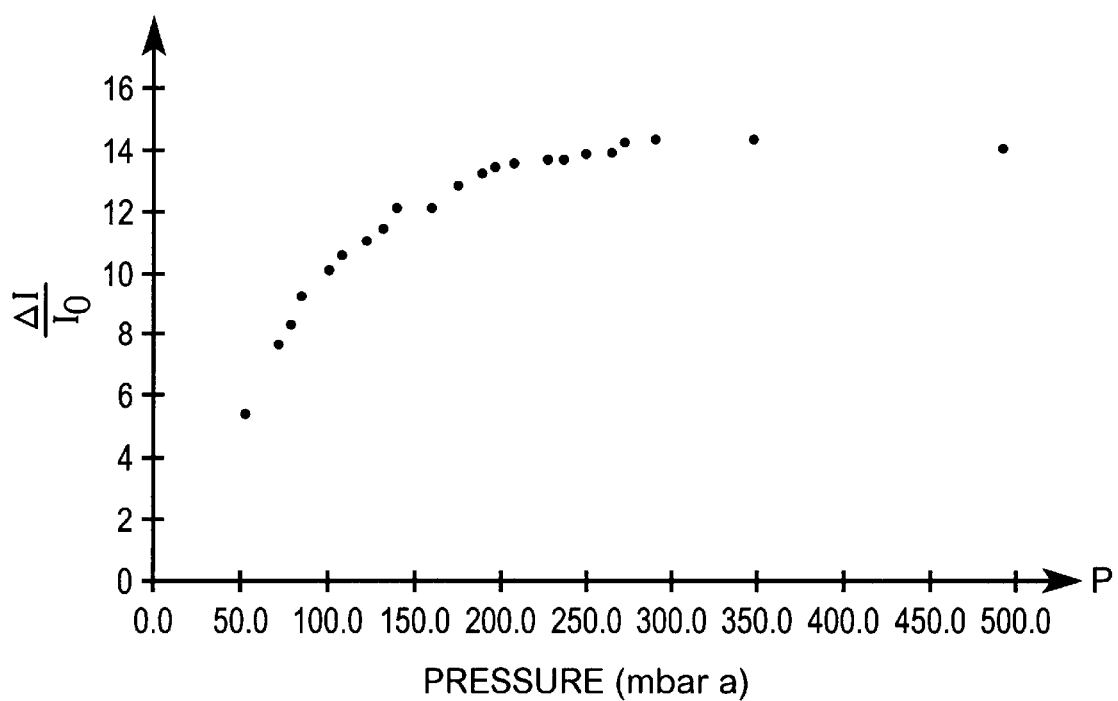
FIG. 3 is a curve showing the variation, as a function of pressure, of the characteristic calculated for quantifying the water molecules present in a gas sample.

Represented in FIG. 3 is the variation, as a function of pressure and for a given amount of impurities, of the ratio $(I_{ana}-I_{ref})/I_{ref}$ making it possible to compute the coefficient of proportionality applied to the characteristic calculated in the course of the analysis so as to obtain the value of the concentration of impurities present in the analysis cell 12.

It is therefore appreciated that the invention just described makes it possible to obtain the value of the concentration of impurities of a gaseous sample relatively directly without having to carry out a prior step of calibrating the analyser, in so far as the tables are used for all the analyses pertaining to the same gas.

Indeed, the user, knowing the gas analysis pressure, can evaluate the water vapour content of his or her sample simply by consulting these tables and, as the case may be, by a fast calculation consisting in dividing the result obtained by the concentration of impurities which was used to compute the tables.

We claim:

1. Process for measuring the amount of impurities in a gas sample filling a laser absorption spectroscopy analysis cell, comprising calculating the value of a characteristic representative of the absorbance of the gas sample, from a measurement of the gas sample at a single given pressure, and quantifying the impurities on the basis of a predetermined law for the variation of the characteristic as a function of the amount of impurities, wherein the characteristic is the ratio of the difference between the luminous intensity ($I_{ana}$) of a light beam transmitted through the gas and the luminous intensity ($I_{ref}$) of the incident beam to the luminous intensity ($I_{ref}$) of the incident beam, the impurities being quantified on the basis of a value of the coefficient of proportionality between the amount of impurities and the characteristic, determined on the basis of a table of variation of the characteristic as a function of pressure, for a given amount of impurities.

2. Process according to claim 1, wherein the light beam is emitted by means of a diode laser according to a range of wavelengths encompassing the wavelength at which the absorption of light by the impurities is a maximum.

3. Process according to claim 2, wherein the luminous intensity of the incident beam is measured by dividing the light beam emitted by the diode laser into an analysis beam intended to be transmitted through the gas sample and a reference beam, and by measuring the intensity ($I_{ref}$) of the reference beam.

4. Process according to claim 1, wherein the table of variation of the characteristic is computed for various types of gas to be analysed by measuring the value of the characteristic at various pressures, for a gas containing a predetermined amount of impurity.

5. Process according to claim 1, wherein the impurities comprise water or water vapor.

6. Process according to claim 1, wherein the gas to be analysed is chosen from gases used in the field of the fabrication of microelectronic components.

7. Device for measuring the amount of impurities in a gaseous sample, for the implementation of a measurement process according to claim 1, comprising a diode laser intended for emitting a light beam according to a range of wavelengths encompassing the wavelength at which the absorption of light by the impurities is a maximum, a light splitter facility adapted for dividing the emitted beam into an analysis beam intended to be transmitted through a laser absorption spectroscopy analysis cell filled with the gaseous sample to be analysed, and into a reference beam, photodetector means intended to receive the analysis and reference beams, and calculation means adapted for calculating the value of a characteristic varying linearly as a function of the amount of impurities and representative of the absorbance of the gas sample, on the basis of a comparison between the intensity, detected by the photodetector means, of the analysis and reference beams, and in that the calculation means include, stored in memory, a set of at least one table of variation of the characteristic as a function of pressure, for a given amount of impurities, with a view to the computation, on the basis of the table, of the coefficient of proportionality to be applied to the calculated value of the characteristic to obtain the amount of impurities.

8. Device according to claim 7, further comprising, stored in memory, a set of tables each corresponding to a type of gas to be analysed.

9. Process according to claim 1, wherein the table of variation of the characteristic is computed for various types of gas to be analysed by measuring the value of the characteristic at various pressures, for a gas containing a predetermined amount of impurity.

10. Process according to claim 2, wherein the table of variation of the characteristic is computed for various types of gas to be analysed by measuring the value of the characteristic at various pressures, for a gas containing a predetermined amount of impurity.

11. Process according to claim 3, wherein the table of variation of the characteristic is computed for various types of gas to be analysed by measuring the value of the characteristic at various pressures, for a gas containing a predetermined amount of impurity.

12. Process according to claim 1, wherein the impurities comprise water or water vapor.

13. Process according to claim 2, wherein the impurities comprise water or water vapor.

14. Process according to claim 3, wherein the impurities comprise water or water vapor.

15. Process according to claim 4, wherein the impurities comprise water or water vapor.

16. Process according to claim 5, wherein the gas to be analysed is chosen from gases used in the field of the fabrication of microelectronic components.

17. Device for measuring the amount of impurities in a gaseous sample, for the implementation of a measurement process according to claim 2, comprising a diode laser intended for emitting a light beam according to a range of wavelengths encompassing the wavelength at which the absorption of light by the impurities is a maximum, a light splitter facility adapted for dividing the emitted beam into an analysis beam intended to be transmitted through a laser absorption spectroscopy analysis cell filled with the gaseous sample to be analysed, and into a reference beam, photodetector means intended to receive the analysis and reference beams, and calculation means adapted for calculating the value of a characteristic varying linearly as a function of the amount of impurities and representative of the absorbance of the gas sample, on the basis of a comparison between the intensity, detected by the photodetector means, of the analysis and reference beams, and in that the calculation means include, stored in memory, a set of at least one table of variation of the characteristic as a function of pressure, for a given amount of impurities, with a view to the computation, on the basis of the table, of the coefficient of proportionality to be applied to the calculated value of the characteristic to obtain the amount of impurities.

18. Device for measuring the amount of impurities in a gaseous sample, for the implementation of a measurement process according to claim 5, comprising a diode laser intended for emitting a light beam according to a range of wavelengths encompassing the wavelength at which the absorption of light by the impurities is a maximum, a light splitter facility adapted for dividing the emitted beam into an analysis beam intended to be transmitted through a laser absorption spectroscopy analysis cell filled with the gaseous sample to be analysed, and into a reference beam, photodetector means intended to receive the analysis and reference beams, and calculation means adapted for calculating the value of a characteristic varying linearly as a function of the amount of impurities and representative of the absorbance of the gas sample, on the basis of a comparison between the intensity, detected by the photodetector means, of the analysis and reference beams, and in that the calculation means include, stored in memory, a set of at least one table of variation of the characteristic as a function of pressure, for a given amount of impurities, with a view to the computation, on the basis of the table, of the coefficient of proportionality to be applied to the calculated value of the characteristic to obtain the amount of impurities.

19. Device for measuring the amount of impurities in a gaseous sample, for the implementation of a measurement process according to claim 6, comprising a diode laser intended for emitting a light beam according to a range of wavelengths encompassing the wavelength at which the absorption of light by the impurities is a maximum, a light splitter facility adapted for dividing the emitted beam into an analysis beam intended to be transmitted through a laser absorption spectroscopy analysis cell filled with the gaseous sample to be analysed, and into a reference beam, photodetector means intended to receive the analysis and reference beams, and calculation means adapted for calculating the value of a characteristic varying linearly as a function of the amount of impurities and representative of the absorbance of the gas sample, on the basis of a comparison between the intensity, detected by the photodetector means, of the analysis and reference beams, and in that the calculation means include, stored in memory, a set of at least one table of variation of the characteristic as a function of pressure, for a given amount of impurities, with a view to the computation, on the basis of the table, of the coefficient of proportionality to be applied to the calculated value of the characteristic to obtain the amount of impurities.

20. Process according to claim 6, wherein the gas to be analysed is chosen from $NH_3$, HCl, HBr, HF, NO, $SiH_4$, $GeH_4$, and perfluorocarbonated gases.

21. Process according to claim 16, wherein the gas to be analysed is chosen from $NH_3$, HCl, HBr, HF, NO, $SiH_4$, $GeH_4$, and perfluorocarbonated gases.

* * * * *